US006846642B2

(12) United States Patent
Mok et al.

(10) Patent No.: US 6,846,642 B2
(45) Date of Patent: Jan. 25, 2005

(54) METHODS OF DETECTING CANCER BASED ON PROSTASIN

(75) Inventors: Samuel C. Mok, Brookline, MA (US); Kwong-Kwok Wong, Sugar Land, TX (US)

(73) Assignees: The Brigham and Women's Hospital, Inc., Boston, MA (US); Battelle Memorial Institute, Richland, WA (US)

(*) Notice: Subject to any disclaimer, the term of this patent is extended or adjusted under 35 U.S.C. 154(b) by 405 days.

(21) Appl. No.: 09/948,094

(22) Filed: Sep. 7, 2001

(65) Prior Publication Data

US 2002/0090625 A1 Jul. 11, 2002

Related U.S. Application Data

(60) Provisional application No. 60/231,166, filed on Sep. 7, 2000.

(51) Int. Cl.[7] .................. G01N 33/50; G01N 33/53; G01N 33/537; G01N 33/574
(52) U.S. Cl. .................. 435/7.23; 435/7.1; 435/7.92; 436/64
(58) Field of Search .................. 435/7.23, 7.92, 435/6, 7.1, 183, 325; 514/2, 12, 1; 530/350; 436/64

(56) References Cited

U.S. PATENT DOCUMENTS

| | | | | |
|---|---|---|---|---|
| 5,604,106 | A | * | 2/1997 | Liotta et al. ............... 435/7.23 |
| 5,695,761 | A | | 12/1997 | Denhardt et al. ......... 424/184.1 |
| 5,712,104 | A | * | 1/1998 | Yamamoto ................. 435/7.92 |
| 5,801,004 | A | * | 9/1998 | Hudson et al. ............ 435/7.23 |
| 5,866,119 | A | | 2/1999 | Bandman et al. .......... 424/94.6 |
| 5,928,883 | A | | 7/1999 | Gleich et al. .............. 435/7.21 |
| 6,414,219 | B1 | | 7/2002 | Denhardt et al. ............. 800/18 |
| 6,686,444 | B2 | | 2/2004 | Ashkar ........................ 530/329 |
| 2002/0039753 | A1 | * | 4/2002 | Chai et al. .................. 435/7.23 |
| 2002/0052308 | A1 | * | 5/2002 | Rosen et al. ................... 514/1 |

OTHER PUBLICATIONS

Coolen et al., "Evaluation of Brain–Type Creatine Kinase in Serum From Patients With Carcinoma," Cancer, vol. 44, pp. 1414–1418 (1979).*
Chen et al., "Prostasin Serine Protease Inhibits Breast Cancer Invasivness and is Transcriptionally REgulated by Promoter DNA Methylation," Int. J. Cancer, vol. 97, pp. 323–329 (2002).*
Derisi, et al., "Use of a cDNA Microarray to Analyse Gene Expression Patterns in Human Cancer," *Nature Genetics* 14:457–460 (1996).
Heid, et al., "Real Time Quantitative PCR," *Genome Research* 6:986–994 (1996).
Kurtz, et al., "Serum Creatine Kinase BB Isoenzyme as a Diagnostic Aid in Occult Small Cell Lung Cancer," *Cancer* 56:562–566 (1985).

Mok, et al., "Molecular Cloning of Differentially Expressed Genes in Human Epithelial Ovarian Cancer," *Gynecologic Oncology* 52:247–252 (1994).
Mok, et al., "SPARC, an Extracellular Matrix Protein with Tumor–Suppressing Activity in Human Ovarian Epithelial Cells," *Oncogene* 12:1895–1901 (1996).
Müeller–Pillasch, et al., "Cloning of a Gene Highly Overexpressed in Cancer Coding for a Novel KH–Domain Containing Protein," *Oncogene* 14:2729–2733 (1997).
Schriml, et al., "Tyramide Signal Amplification (TSA)–FISH Applied to Mapping PCR–Labeled Probes Less than 1 kb in Size," *Biotechniques* 27:608–613 (1999).
Schummer, et al., "Comparative Hybridization of an Array of 21 500 Ovarian cDNAs for the Discovery of Genes Overexpressed in Ovarian Carcinomas," *Gene* 238:275–385 (1999).
Sharp, et al., "Tumor Cells are the Source of Osteopontin and Bone Sialoprotein Expression in Human Breast Cancer," *Laboratory Investigation* 79:869–877 (1999).
Szala, et al., "Molecular Cloning of cDNA for the Carcinoma–Associated Antigen GA733–2," *Proc. Natl. Acad. Sci.* 87:3542–3546 (1990).
Tuck, et al., "Osteopontin Induces Increased Invasiveness and Plasminogen Activator Expression of Human Mammary Epithelial Cells," *Oncogene* 18:4237–4246 (1999).
Wang, et al., "Monitoring Gene Expression Profile Changes in Ovarian Carcinomas Using cDNA Microarray," *Gene* 229:101–108 (1999).
Yu, et al., "Molecular Cloning, Tissue–Specific Expression, and Cellular Localization of Human Prostasin in mRNA," *Journal of Biological Chemistry* 270:13483–13489 (1995).
Yu, et al., "Prostasin Is a Novel Human Serine Proteinase from Seminal Fluid," *Journal of Biological Chemistry* 269:18843–18848 (1994).
Berteau, et al., "Prostasin mRNA to Detect Prostate Cells in Blood of Cancer Patients," *Clin. Chem. Lab. Med.* 37:S119 (1999).
Chen, et al., "Down–Regulation of Prostasin Serine Protease: A Potential Invasion Suppressor in Prostate Cancer," *Prostate* 48:93–103 (2001).
Hooper, et al., "Testisin, a New Human Serine Proteinase Expressed by Premeiotic Testicular Germ Cells and Lost in Testicular Germ Cell Tumors," *Cancer Res.* 59:3199–3205 (1999).
Hooper, et al., "Localization, Expression and Genomic Structure of the Gene Encoding the Human Serine Protease Testisin," *Biochimica et Biophysica Acta* 1492:63–71 (2000).

(List continued on next page.)

*Primary Examiner*—James Housel
*Assistant Examiner*—Zachariah Lucas
(74) *Attorney, Agent, or Firm*—Michael A. Sanzo; Fitch Even, Tabin & Flannery

(57) ABSTRACT

The present invention is directed to diagnostic methods based upon the expression of the protein prostasin. In particular, it is concerned with assays performed on women to determine their risk of ovarian cancer.

8 Claims, No Drawings

OTHER PUBLICATIONS

Yiu, et al., "Prostasin, a Potential Serum Marker for the Early Detection of Ovarian Cancer" *Proceedings of the American Association for Cancer Research Annual* 42:744 (2001).

Ali, et al., "Intercellular Cell Adhesion Molecule–1, Vascular Cell Adhesion Molecule–1, and Regulated on Activation Normal T Cell Expressed and Secreted Are Expressed by Human Breast Carcinoma Cells and Support Eosinophil and Activation," *Am. J. Path.* 157:313–321 (2000).

Alper, "Turning Sweet on Cancer," *Science* 301:159–160 (2003).

Barker, et al., "Eosinophil Cationic Protein cDNA, Comparison with Other Toxic Cationic Proteins and Ribonucleases," *J. Immunol.* 143:952–955 (1989).

Bast, et al., "A Radioimmunoassay Using a Monoclonal Antibody to Monitor the Course of Epithelial Ovarian Cancer," *N. Engl. J. Med.* 309:883–887 (1983).

Beintema, et al., "Amino Acid Sequence of the Nonsecretory Ribonuclease of Human Urine," *Biochemistry* 27:4530–4538 (1988).

Blumenthal, et al., "Degranulating Eosinophils in Human Endometriosis," *Am. J. Path.* 156:1581–1588 (2000).

Cheung, et al., "Identify Metastasis–Associated Genes in Hepatocellular Carcinoma through Clonality Delineation for Multinodular Tumor," *Cancer Res.* 62:4711–4721 (2002).

Cramer, et al., "Carotenoids, Antioxidants and Ovarian Cancer Risk in Pre– and Postmenopausal Women," *Int. J. Cancer* 94:128–134 (2001).

Daly, et al., "The Search for Predictive Patterns in Ovarian Cancer: Proteomics Meets Bioinformatics," *Cancer Cell* 1:111–112 (2002).

Denhardt, et al., "Osteopontin: A Protein with Diverse Functions," *FASEB J.* 7:1475–1482 (1993).

Dorta, et al., "Tumor–Associated Tissue Eosinophilia as a Prognostic Factor in Oral Squamous Cell Carcinomas," *Histopathology* 41:152–157 (2002).

Fernández–Aceñero, et al., "Prognostic Influence of Tumor–Associated Eosinophilic Infiltrate in Colorectal Carcinoma," *Cancer* 88:1544–1548 (2000).

Fish, et al., "Changes in Serum Acute Phase Proteins in Ovarian Cancer Patients Receiving Cis–Diamminedichloroplatinum (CDDP) Infusion Therapy," *Clinical Biochem.* 17:39–41 (1984).

Fish, et al., "Serum Haptoglobin and α1–Acid Glycoprotein as Indicators of the Effectiveness of cis–Diamminedichloroplatinum (CDDP) in Ovarian Cancer Patients—a Preliminary Report," *Eur. J. Cancer Clin. Oncol.* 20:625–630 (1984).

Giachelli, et al., "Molecular and Cellular Biology of Osteopontin," *Trends Cardiovasc. Med.* 5:88–95 (1995).

Gingrich, et al., "Metastatic Prostate Cancer in a Transgenic Mouse," *Cancer Res.* 56:4096–4102 (1996).

Hakomori, "Glycosylation Defining Cancer Malignancy: New Wine in an Old Bottle," *Proc. Natl. Acad. Sci. USA* 99:10231–10233 (2002).

Hamann, et al., "Sequence of Human Eosinophil–Derived Neurotoxin cDNA: Identity of Deduced Amino Acid Sequence with Human Nonsecretory Ribonucleases," *Gene* 83:161–167 (1999).

Hamann, et al., "Structure and Chromosome Localization of the Human Eosinophil–Derived Neurotoxin and Eosinophil Cationic Protein Genes: Evidence for Intronless Coding Sequences in the Ribonuclease Gene Superfamily," *Genomics* 7:535–546 (1990).

Hawley, et al., "Cancer Cells Release a Covalent Complex Containing Disulfide–Linked Domains from Urinary Plasminogen Activator, Neural Cell Adhesion Molecule, and Haptoglobin α and β Chains," *Arch. Biochem. Biophys.* 345:289–298 (1997).

Kakugawa, et al., "Up–Regulation of Plasma Membrane–Associated Ganglioside Sialidase (Neu3) in Human Colon Cancer and Its Involvement in Apoptosis Suppression," *Proc. Natl. Acad. Sci. USA* 99:10718–10723 (2002).

Kibel, et al., "Loss of Heterozygosity at 12P12–13 in Primary and Metastatic Prostate Adenocarcinoma," *J. Urol.* 164:192–196 (2000).

Kiefer, et al., "The cDNA and Derived Amino Acid Sequence for Human Osteopontin," *Nuc. Ac. Res.* 17:3306 (1989).

Kim, et al., "Osteopontin as a Potential Diagnostic Biomarker for Ovarian Cancer," *JAMA* 287:1671–1679 (2002).

Ko, et al., "Haptoglobin Typing and Quantitation in Normal Chinese Females and Gynecologic Cancer Patients," *Chinese J. Microbiol. Immunol.* 13:149–157 (1980).

Ko, et al., "Haptoglobin Typing and Quantitation in Normal Chinese Females and Gynecologic Cancer Patients," *Chinese J. Microbiol. Immunol.* 13:149–157 (1980) Abstract; Database Medline, Accession No. 81089629.

Kodama, et al., "Large Cell Carcinoma of the Lung Associated with Marked Eosinophilia," *Cancer* 54:2313–2317 (1984).

Mills, et al., "Future for Ovarian Cancer Screening: Novel Markers From Emerging Technologies of Transcriptional Profiling and Proteomics," *J. Natl. Cancer. Inst.* 93:1437–1439 (2001).

Mok, et al., "Prostasin, a Potential Serum Marker for Ovarian Cancer: Identification Through Microarray Technology," *J. Natl. Cancer Inst.* 93:1458–1464 (2001).

Oldberg, et al., "Cloning and Sequence Analysis of Rat Bone Sialoprotein (Osteopontin) cDNA Reveals an Arg–Gly–Asp Cell–Binding Sequence," *Proc. Natl. Acad. Sci. USA* 83:8819–8823 (1986).

Oldberg, et al., "Identification of a Bone Sialoprotein Receptor in Osteosarcoma Cells," *J. Biol. Chem.* 263:19433–19436 (1988).

Pastrňák, et al., "Local Eosinophilia in Stroma of Tumors Related to Prognosis," *Neoplasma* 31:323–326 (1984).

Patarca, et al., "Differential Induction of Interferon γ Gene Expression after Activation of CD4+ Cells by Conventional Antigen and Mls Superantigen," *Proc. Natl. Acad. Sci. USA* 88:2736–2739 (1991).

Peng, et al., "Proteomics: The Move to Mixtures," *J. Mass Spectrom.* 36:1083–1091 (2001).

Petricoin, et al., "Use of Proteomic Patterns in Serum to Identify Ovarian Cancer," *Lancet* 359:572–577 (2002).

Piva, et al., "Interleukin–6 Differentially Stimulates Haptoglobin Production by Peritoneal and Endometriotic Cells in Vitro: A Model for Endometrial–Peritoneal Interaction in Endometriosis," *J. Clin. Endocrinol. Metab.* 86:2553–2561 (2001).

Ren, et al., "Reduced Lysyl Oxidase Messenger RNA Levels in Experimental and Human Prostate Cancer," *Cancer Res.* 58:1285–1290 (1998).

Rosenberg, et al., "Molecular Cloning of the Human Eosinophil–Derived Neurotoxin: A Member of the Ribonuclease Gene Family," *Proc. Natl. Acad. Sci. USA* 86:4460–4464 (1989).

Sakakibara, et al., "A Putative Mouse Oocyte Maturation Inhibitory Protein from Urine of Pregnant Women: N–Terminal Sequence Homology with Human Nonsecretory Ribonuclease," *Chem. Pharm. Bull.* 39:146–149 (1991).

Sakakibara, et al., "Characterization of a Unique Nonsecretory Ribonuclease from Urine of Pregnant Women," *J. Biochem.* 111:325–330 (1992).

Samoszuk, et al., "New Marker for Blood Vessels in Human Ovarian and Endometrial Cancers," *Clin. Cancer Res.* 2:1867–1871 (1996).

Samoszuk, et al., "Occult Deposition of Eosinophil Peroxidase in a Subset of Human Breast Carcinomas," *Am. J. Pathol.* 148:701–706 (1996).

Samoszuk, "Eosinohils and Human Cancer," *Histol. Histopathol.* 12:807–812 (1997).

Schleich, et al.,"Serum Ribonuclease Activity in Patients with Ovarian Tumors," *Eur. J. Gynaec. Oncol.* 7:76–81 (1986).

Schleich, et al., "Ovarian Carcinoma: Increase in Clinical Validity by Simultaneous Determination o f SRA and CA 125," *J. Cancer Res. Clin. Oncol.* 113:603–607 (1987).

Schneider, et al., "Osteopontin But Not Osteonectin Messenger RNA Expression Is a Prognostic Marker in Curatively Resected Non–Small Cell Lung Cancer," *Clin. Cancer Res.* 10:1588–1596 (2004).

Schummer, et al.,"Comparative Hybridization of an Array of 21 500 Ovarian cDNAs for the Discovery of Genes Overexpressed in Ovarian Carcinomas," *Gene* 238:375–385 (1999).

Schwartz, "The Hypereosinophilic Syndrome and the Biology of Cancer," *N. Engl. J. Med.* 348:1199–1200 (2003).

Senger, et al., "Elevated Expression of Secreted Phosphoprotein I (Osteopontin, 2ar) as a Consequence of Neoplastic Transformation," *Anticancer Res.* 9:1291–1300 (1989).

Sheid, et al., "Plasma R Ribonuclease, A Marker for the Detection of Ovarian Cancer," *Cancer* 39:2204–2208 (1977).

Shindo, "Haptoglobin Subtyping with Anti–Haptoglobin. Alpha.Chain Antibodies," *Electrophoresis* 11:483–488 (1990), see especially Abstract; Database Caplus, Accession No. 1990:548290, (Sch. Med. Akita Univ., Hondo, Japan.

Smith, et al., "Molecular Cloning and a Tumor Promoter–Inducible mRNA Found in JB6 Mouse Epidermal Cells: Induction Is Stable at High, but Not at Low, Cell Densities," *J. Cell. Biochem.* 34:13–22 (1987).

Suster, "Tumors of the Skin Composed of Large Cells with Abundant Eosinophilic Cytoplasm," *Semin. Diagn. Pathol.* 16:162–177 (1999).

Thompson, et al., "Increased Fucosylation and Other Carbohydrate Changes in Haptoglobin in Ovarian Cancer," *Cancer Letters* 66:43–48 (1992).

Vlahou, et al., "Development of a Novel Proteomic Approach for the Detection of Transitional Cell Carcinoma of the Bladder in Urine," *Am. J. Pathol.* 158:1491–1502 (2001).

Ye, et al., "Identification and Validation of Urinary Biomarkers for Early Stage of Ovarian Cancer by Multiple Proteomic Approaches," *Proc. Am. Assoc. Cancer Res.* 45:915 (abstract 3964 (2004)).

Ye, et al., "Haptoglobin–α Subunit as Potential Serum Biomarker in Ovarian Cancer: Identification and Characterization Using Proteomic Profiling and Mass Spectrometry," *Clin. Cancer Res.* 9:2904–2911 (2003).

Zhou, et al., "Biomarkers Associated with Prostate Cancer Progression," *J. Cell. Biochem. Suppl.* 19:208–216 (1994).

\* cited by examiner

METHODS OF DETECTING CANCER BASED ON PROSTASIN

CROSS REFERENCE TO RELATED APPLICATIONS

The present application claims the benefit of U.S. provisional application No. 60/231,166, filed on Sep. 7, 2000 (now abandoned).

FIELD OF THE INVENTION

The present invention is in the field of tumor cell markers and is particularly concerned with methods of detecting cancer by assaying samples for prostasin. In its most preferred embodiment, the invention is directed to methods in which serum or plasma samples obtained from a woman are assayed to assess her risk of developing ovarian cancer.

BACKGROUND OF THE INVENTION

Ovarian cancer is the fifth leading cause of death from cancer in U.S. women. In most instances, a diagnosis is not made until the cancer is in an advanced state; at a time when the five year survival rate of patients is only about 28% (Ries, et al., SEERC Cancer Stat. Rev. 1973–1995 (1998)). In contrast, the five year survival rate for women diagnosed with localized disease is about 95%. These statistics provide an incentive to search for tests that can be used to identify ovarian cancer at an early stage.

The protein prostasin was originally isolated from human seminal fluid and is present at high levels in the prostate gland (Yu, et al., *J. Biol. Chem.* 270:13483–13489 (1995); Heid, et al., *Genome Res.* 6:986–994 (1996)). It is expressed to a lesser extent in the kidney, liver, pancreas, salivary gland, lung and colon (Yu, et al.) *J. Biol.* 270:13483–13489 (1995); Yu, et al., *J. Biol. Chem.* 269:18843–18848 (1994)). Its function in these tissues has not yet been determined and a clear association between prostasin and cancer has not been established.

SUMMARY OF THE INVENTION

The present invention is based upon the discovery that prostasin can be used as a marker for identifying patients who have, or are likely to develop, certain types of cancer. In particular, it has been found that prostasin is elevated in the serum of women with ovarian cancer.

In its first aspect, the invention is directed to a method of determining whether a human subject has, or is likely to develop, a malignant growth. A biological sample is obtained from the subject and then assayed to determine the concentration of prostasin protein or mRNA present. The results obtained from this assay are then compared with the results obtained using one or more comparable biological control samples. In general, control samples will be of the same type as test samples but will be obtained from a population not believed to have a malignant growth. Alternatively, controls may simply be the normal concentration range of prostasin in comparable samples from the general population. Once assays have been completed, a conclusion may be drawn that the subject being examined has or is likely to develop a malignant growth if the prostasin concentration present in the test sample is significantly higher than in the control sample. As used herein, the term "significantly higher" means that a difference meets the criteria for significance accepted in the art using standard statistical methods. A significantly higher risk means a probability of having cancer which is greater than that of the population as a whole and which warrants further diagnostic testing.

In general, biological samples will be samples of either serum or plasma and prostasin levels will be determined using an ELISA type assay. An example of a specific assay that can be used is set forth in the Examples section below. Most preferably, tests are performed on women for the purpose of determining whether they are at increased risk of having ovarian cancer. It is expected however that the assay will also be applied to other types of cancers such as cancer of the breast, prostate, lung, colon and pancreas. In another embodiment, assays are performed using tissue samples obtained by biopsy. The prostasin levels present in the tissue may be evaluated by ELISA or prostasin mRNA levels may be determined by reverse transcription PCR.

In a more specific aspect, the invention is directed to a method of determining the likelihood that a woman has or is likely to develop ovarian cancer by obtaining a test sample of plasma or serum from the woman and determining the concentration of prostasin present in the sample. The results obtained are compared with results from a control sample and a conclusion is drawn that the woman has or is likely to develop ovarian cancer if the concentration determined for the test sample is significantly higher than the concentration in the controls. Most preferably, the test will be performed using the ELSA discussed above. This same method can also be carried out by assaying a test sample of serum or plasma and concluding that an increased likelihood of ovarian cancer exists if the concentration of prostasin is greater than 10 micrograms per ml. or, in a more stringent test, if the concentration is greater than 12 micrograms per ml.

The assays of prostasin discussed above may either be used alone or in conjunction with other diagnostic tests. In particular, the assays may be used in conjunction with other methods in which the concentration of a tumor marker is determined. Such markers may include, for example, prostate specific antigen, CEA, alpha-fetoprotein and, in the case of tests for ovarian cancer, CA 125.

DETAILED DESCRIPTION OF THE INVENTION

The discovery of a correlation between prostasin concentration and ovarian cancer is an outgrowth of more extensive studies on genes that are either over- or underexpressed in cancerous ovarian epithelial cells. Numerous genes were identified which may also be used as markers and which are listed in the tables found in the Examples section below. Nevertheless, the strongest correlation has been found for prostasin which also has the advantage of being detectable in biological samples that can be readily obtained, i.e., samples of plasma or serum. The other genes that have been correlated with the transformation of ovarian cells have all been described in the literature and methods are known for assaying the concentration of each.

In the case of prostasin, the full length amino acid and nucleotide sequence of the human protein and gene are known in the art. These may be found as GenBank accession number L41351. The full length cDNA is 1834 nucleotides long, with the coding sequence running from nucleotide 229 to 1260. The sequence is also disclosed herein as SEQ ID NO: 1 (DNA sequence) and SEQ ID NO:2, amino acid sequence). The protein may be purified using procedures described in the art or, alternatively, it can be chemically synthesized.

Assays for prostasin expression may be determined by RT-PCR using primers selected from the known gene sequence. Specific examples of primers that can be used for successfully carrying out RT-PCR are described in detail in the Examples section. ELISA assays are also disclosed in which the antibody described by Yu, et al. is used. However, other types of immunoassays can also be successfully used and antibodies may be produced using standard methods.

Antibodies that bind specifically to prostasin are defined for the purposes of the present invention as those that have at least a 100 fold greater affinity for prostasin then for any other similar undenatured protein. The process for producing such antibodies may involve either injecting the prostasin protein itself into an appropriate animal or injecting short peptides made to correspond to different regions of prostasin. The peptides injected should be a minimum of 5 amino acids in length and should be selected from regions believed to be unique to the protein. Methods for making and detecting antibodies are well known to those of skill in the art has evidenced by standard reference works such as: Harlow, et al., *Antibodies, Laboratory Manual*, Cold Spring Harbor Laboratory, N.Y. (1988); Klein, *Immunology: The Science of Self-Nonself Discrimination* (1982); Kennett, et al., *Monoclonal Antibodies and Hybridomas: A New Dimension in Biological Analyses* (1980); and Campbell, "Monoclonal Antibody Technology," in: *Laboratory Techniques in Biochemistry and Molecular Biology* (1984).

"Antibody," as used herein is meant to include intact molecules as well as fragments which retained the ability to bind antigen (e.g., Fab and F(ab')$_2$ fragments). These fragments are typically produced by proteolytically cleaving intact antibodies using enzymes such as a papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975). In general, this technology involves immunizing an animal, usually a mouse, with either intact prostasin or a fragment derived from prostasin. The splenocytes of the immunized animals are extracted and fused with suitable myeloma cells, e.g., SP$_2$O cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to prostasin.

The antibodies or fragments of antibodies of the present invention may be used to detect to the presence of the prostasin protein in any of a variety of immunoassays. For example, antibodies may be used in radioimmunoassays or immunometric assays, also known as "two-site" or "sandwich assays" (see Chard, "Introduction to Radioimmune Assay and Related Techniques," in: *Laboratory Techniques in Biochemistry and Molecular Biology*, North Holland Publishing Co., N.Y. (1978)). In a typical immunometric assay, a quantity of unlabelled antibody is bound to a solid support that is insoluble in the fluid being tested, e.g., blood lymph, cellular extracts, etc. After the initial binding of antigen to immobilized antibody, a quantity of detectably labeled second antibody (which may or may not be the same as the first) is added to permit the detection and/or quantitation of bound antigen (see e.g., *Radioimmune Assay Method*, Kirkham, et al., ed. pp. 199–206, E&S Livingston, Edinburgh (1970)). Many variations of these types of assays are known in the art and may be employed for the detection of prostasin.

If desired, antibodies to prostasin may also be used in the purification of the protein (see generally, Dean, et al., *Affinity Chromatography, A Practical Approach*, IRL Press (1986)). Typically, antibody is immobilized on a chromatographic matrix such as Sepharose 4B. The matrix is then packed into a column and the preparation containing prostasin is passed through under conditions that promote binding, e.g., under conditions of low salt. The column is then washed and bound prostasin is eluted using a buffer that promotes disassociation of antibody, e.g., a buffer having an altered pH or salt concentration. The eluted prostasin may be transferred into a buffer of choice, e.g., by dialysis, and either stored or used directly.

The same basic techniques described above in connection with prostasin may also be adapted to any of the other genes or proteins identified herein as being associated with ovarian cancer. Also, it should be readily apparent that the same assays may be used in connection with other types of cancer as well, especially those of the pancreas, prostate, kidney, and lungs.

EXAMPLES

Example 1

Differentially Exposed Genes from Ovarian Cancer Cells

A. Materials and Methods

Cell Culture

Cultures of normal human ovarian surface epithelial cells (HOSE) were established by scraping the HOSE cells from the ovary and growing them in a mixture of Medium 199 and MCDB105 supplemented with 10% fetal calf serum (Mok, et al., *Gynecol. Oncol.* 52:247–52, (1994)). The seven HOSE cells used were HOSE17, HOSE636, HOSE642, HOSE695, HOSE697, HOSE713, and HOSE726. Ovarian cancer cell lines used were OVCA3, OVCA420, OVCA432, OVCA433, OVCA633, SKOV3, and ALST.

Microarray Probe and Hybridization

MICROMAX™ human cDNA microarray system I (NEN Life Science Products, Inc., Boston, Mass.), which contains 2400 known human cDNAs on a 1×3" slide, was used in this study. Microarray probe and hybridization were performed as described in the instruction manual. In brief, biotin-labeled cDNA was generated from 3 µg total RNA, which was pooled from HOSE17, HOSE636 and HOSE642. Dinitrophenyl (DNP)-labeled cDNA was generated from 3 µg total RNA that was pooled from ovarian cancer cell lines OVCA420, OVCA433 and SKOV3. Before the cDNA reaction, an equal amount of RNA control was added to each batch of the RNA samples for normalization during data analysis. Biotin-labeled and DNP-labeled cDNA were mixed, dried and resuspended in 20 µl hybridization buffer, which was added to the cDNA microarray and covered with a coverslip. Hybridization was carried out overnight at 65° C. inside a hybridization cassette.

Post Hybridization and Cyanine-3 (Cy3™) and Cyanine-5 (Cy5™) Tyramide Signal Amplification (TSA)

After hybridization, microarrays were washed with 30 ml 0.5×SSC, 0.01% SDS, and then 30 ml 0.06×SSC, 0.01% SDS. Finally the microarray was washed with 0.06×SSC. Hybridization signal from biotin-labeled cDNA was amplified with streptavidin-horseradish peroxidase and Cy5™-tyramide, while hybridization signal from DNP-labeled cDNA was amplified with anti-DNP-horseradish peroxidase and Cy3™-tyramide. After signal amplification and post-hybridization wash, cDNA microarray was air-dried and detected with a laser scanner.

Image Acquisition and Data Analysis

Cy3 signal was derived from ovarian cancer cells and Cy5 signal was derived from HOSE cells. Laser detection of the Cy3 and Cy5 signal on the microarray was acquired with a confocal laser reader, ScanArray3000 (GSI Lumonics, Watertown, Mass.). Separate scans were taken for each fluor at a pixel size of 10μ. cDNA derived from the control RNA hybridized to 12 specific spots within the microarray. Cy3 and Cy5 signals from these 12 spots should theoretically be equal and were used to normalize the different efficiencies in labeling and detection with the two fluors. The fluorescence signal intensities and the Cy3/Cy5 ratios for each of the 2400 cDNAs were analyzed by the software Imagene 3.0 (Biodiscovery Inc, Los Angeles, Calif.).

Real-time Quantitative RT-PCR

Real-time PCR was performed in duplicate using primer sets specific to GA733-2, osteopontin, prostasin, creatine kinase B, CEA, KOC and a housekeeping gene, cyclosporin, in an ABI PRISM 5700 Sequence Detector. RNA was first extracted form normal ovarian epithelial cell cultures (HOSE695, 697, 713, and 726) and six ovarian carcinoma cell lines (OVCA3, OVCA432, OVCA433, OVCA633, SKOV3 and ALST). cDNA were generated from 1 μg total RNA using the TaqMan reverse transcription reagents containing 1×TaqMan RT buffer, 5.5 mM $MgCl_2$, 500 μM dNTP, 2.5 μM random hexamer, 0.4 U/μl RNase inhibitor, 1.25 U/μl MultiScribe reverse transcriptase (PE Applied Biosystems, Foster City, Calif.) in 100 μl. The reaction was incubated at 25° C. for 10 min, 48° C. for 30 min and finally at 95° C. for 5 min. 0.51 μl of cDNA was used in a 20 μl PCR mix containing 1×SYBR PCR buffer, 3 mM $MgCl_2$, 0.8 mM dNTP, and 0.025 U/μl AmpliTaq Gold (PE Applied Biosystems, Foster City, Calif.). Amplification was then performed with denaturation for 10 min at 95° C., followed by 40 PCR cycles of denaturation at 95° C. for 15 sec and annealing/extension at 60° C. for 1 min. The changes in fluorescence of SYBR Green I dye in every cycle was monitored by the ABI5700 system software, and the threshold cycle ($C_T$) for each reaction was calculated. The relative amount of PCR products generated from each primer set was determined based on the threshold cycle or $C_T$ value. Cyclosporin was used for the normalization of quantity of RNA used. Its $C_T$ value was then subtracted from that of each target gene to obtain a $\Delta C_T$ value. The difference ($\Delta\Delta C_T$) between the $\Delta C_T$ values of the samples for each gene target and the $\Delta C_T$ value of the calibrator (HOSE726) was determined. The relative quantitative value was expressed as $2^{-\Delta\Delta C_T}$.

B. Results and Discussion

The MICROMAX System

The MICROMAX system allows the simultaneous analysis of the expression level of 2400 known genes. The use of TSA signal amplification in the system after hybridization reduces the amount of total RNA needed to a few micrograms which is about 20–100 times less than currently used methods. The details of TSA have been described previously for chromosome mapping of PCR-labeled probes less than 1 kb by FISH (Schriml, et al., *Biotechniques* 27:608–611, (1999)). In this study, 30 putative differentially overexpressed genes (excluding 9 ribosomal genes) were identified in ovarian cancer cell lines (Table 1). Using high density cDNA array on membranes, Schummer et al. (Schummer, et al., *Gene* 238:375–385, (1999)) has identified 32 known genes that exhibit a tumor-to-HOSE ratios of more than 2.5-fold. Fourteen of these 32 genes were present in the MICROMAX cDNA microarray but only five of them were present at more than 3-fold.

Biotin-labeled cDNA was made from ovarian cancer cell lines, while DNP-labeled cDNA was made from HOSE cells. The differential TSA amplification of the hybridization signal depends on the use of a Steptavidin-HRP conjugate or anti-DNP-HRP conjugate in a sequential step. At each step, cyanine-5-Tyramide or cyanine-3-Tyramide can be added and the HRP will then catalyze the deposit of Cy3 or Cy5 onto the hybridized cDNA nonspecifically. As a result, either Cy3 or Cy5 signals can be used for the cDNA derived from ovarian cancer cell lines, and vice versa for HOSE cells. Thus, it is not necessary to make two different sets of probes to compare the effect of Cy3 or Cy5 fluorescence as a result of their differences in extinction coefficients and quantum yields. Cy3 and Cy5 signals on the processed slides were stable for more than 6 months.

Normalization of Signals

The MICROMAX system has 3 nonhuman genes as internal controls. Each of the control genes is spotted 4 times on the microarray. Equal amounts of polyA RNA derived from these control genes were spiked into the total RNA samples derived from both HOSE and ovarian cancer cell lines during cDNA synthesis. Thus, hybridization signals from these control genes in two RNA samples should theoretically be the same. The Cy3 to Cy5 ratios for these control genes varied from 0.4 to 4.0 and the average ratio was 1.5±1.1. From a prior microarray analysis of human cancer cells, 88 genes have been identified to express at relatively constant levels in many cell types (DeRisi, et al., *Nat. Genet.* 14:457–60, (1996)). The MICROMAX microarray also contains 58 of these 88 genes and 21 of these genes with signal to background ratio more than 3-fold were analyzed (Table 2). The ratios varied from 0.23 to 5.22. The average ratio is 1.6±1.5. Thus, the result of internal control RNA for normalizing signal was similar to that of genes that express at a relatively constant level in different cell types.

Effect of Background Signal on the Identification of Differentially Expressed Genes In the present study, 1357 of the 2400 genes on the microarray have Cy3 signals (from ovarian cancer cell lines) that were at least two-fold higher than the background, and 740 genes have Cy3 signals that were at least three-fold higher than the background. After post-hybridization washes, there was still significant background intensity for the Cy3 signal but very low background for Cy5. Subsequently, the microarray was washed again in 30 ml TNT buffer at 42° C. for 20 minutes instead of at room temperature, followed by 30 ml of 0.006×SSC for 1 minute. The washed microarray was then dried and re-scanned. This process was repeated several times until the number of genes with signal to background ratios at least 3-fold remained the same. The extensive washing steps decreased the background intensity significantly, but there was no obvious changes in the signal intensity. As a result, the number of genes with at least 3-fold signal to background ratios increased from 740 to 791 genes. Moreover, the differential expression ratios, in general, also increased (Table 1 to Table 2). More importantly, after the extensive washing, we were able to detect the differential expression of two weakly expressed genes, thiol-specific antioxidant protein (4.5-fold) and elongation factor-1-β (9.7-fold), which were previously identified by Schummer et al. Thus, the extensive post-hybridization washing and re-scanning of signals may be necessary to decrease background signal especially in the case of differentially expressed genes with low expression levels.

Confirmation of Differential Expression by Real-time Quantitative PCR

To further validate differential expression, five interesting genes were chosen, GA733-2, osteopontin, koc, prostasin, and creatine kinase B, for real-time PCR analysis. All these genes are either surface antigens or secreted proteins. Thus, they may be useful as tumor markers for ovarian cancer. GA733-2 is a cell surface 40-kDa glycoprotein associated with human carcinomas of various origins (Szala, et al., *Proc. Natl. Acad. Sci. USA* 87:3542–6, (1990)). Osteopontin is a secreted glycoprotein with a conserved Arg-Gly-Asp (RGD) integrin-binding motif and is expressed predominantly in bone, but has also been found in breast cancer and thyroid carcinoma with enhanced invasiveness (Sharp, et al., *Lab. Investigat.* 79:869–877, (1999), Tuck, et al., *Oncogene* 18:4237–4246, (1999)). Prostasin is a novel secreted serine proteinase which was originally identified in seminal fluid (Yu, et al., *J. Biol. Chem.* 269:18843–8, (1994)). The koc transcript is highly over-expressed in pancreatic cancer cell lines as well as in pancreatic cancer. It is speculated that koc may assume a role in the regulation of tumor cell proliferation by interfering with transcriptional and or posttranscriptional processes (Mueller-Pillasch, et al., *Oncogene* 14:2729–33, (1997)). Creatine kinase B is a serum marker associated with renal carcinoma and lung cancer (Kurtz, et al., *Cancer* 56:562–6, (1985), Takashi, et al., *Urologia Internationalis* 48:144–8, (1992)). Two randomly selected genes, CEA and RGS, were used as negative controls.

The results showed that all the tested ovarian cancer cell lines expressed higher levels of GA733-2. However, osteopontin, prostasin, KOC and creatine kinase B were over-expressed in only some of the cancer cell lines. Since we were using pools of RNA, the differential expression that was observed is an average of the gene expression from 3 independent HOSE cells or 3 different cancer cell lines. This strategy allows us to capture genes that overexpress in either some or all of the cell lines. Genes that only overexpress in some of the ovarian cancer cell lines may be useful for molecular classification of ovarian cancer cells. Since as little as 10 pg cDNA is enough for real-time quantitative RT-PCR reaction, RNA extracted from microdissected tissue would be enough for thousands of such real-time quantitative RT PCR analyses.

TABLE 1

List of genes differentially over-expressed in ovarian cancer cells more than 10-fold.

| Accession # | Description | Before extensive washing (Cy3/Cy5) | After extensive washing (Cy3/Cy5) | Cy3 signal intensity |
|---|---|---|---|---|
| M33011 | carcinoma-associated antigen GA733-2 | 472 | 444 | 1249 |
| J04765 | Osteopontin | 156 | 184 | 11851 |
| L41351 | Prostasin | 44 | 170 | 3172 |
| L19783 | GPI-H | 4 | 88 | 916 |
| U96759 | Von Hippel-Lindau binding protein (VBP-1) | 60 | 59 | 1377 |
| M57730 | B61 | 20 | 49 | 5514 |
| L33930 | CD24 signal transducer and 3' region | 24 | 47 | 26722 |
| D55672 | hnRNP D | 45 | 44 | 950 |
| U97188 | Putative RNA binding protein KOC | 223 | 38 | 3599 |
| L19871 | ATF3 | 9 | 37 | 3507 |
| J04991 | p18 | 15 | 34 | 9914 |
| D00762 | mRNA for proteasome subunit HC8 | 17 | 29 | 4703 |
| U17989 | Nuclear autoantigen GS2NA | 5 | 28 | 721 |
| U43148 | Patched homolog (PTC) | 10 | 28 | 4155 |
| AF010312 | Pig7(PIG7) | 13 | 23 | 17379 |
| M80244 | E16 | 18 | 21 | 4180 |
| X99802 | mRNA for ZYG homologue | 14 | 21 | 2086 |
| U05598 | Dihydrodioldehydrogenase | 10 | 18 | 21595 |
| L47647 | Creatine kinase B. | 7 | 18 | 787 |
| M55284 | Protein kinase C-L (PRKCL) | 7 | 16 | 863 |
| X15722 | mRNA for glutathione reductase | 23 | 14 | 794 |
| 554005 | Thymosin beta-10 | 6 | 13 | 1476 |
| AB006965 | mRNA for Dnmlp/Vpslp-like protein | 7 | 13 | 4183 |
| M83653 | Cytoplasmic phosphotyrosyl protein Phosphatase | 6 | 13 | 2156 |
| X12597 | mRNA for high mobility group-1 protein (HMG-1) | 7 | 12 | 2785 |
| M18112 | poly(ADP-ribose) polymerase | 6 | 12 | 9277 |
| U56816 | Kinase Mytl (Mytl) | 4 | 11 | 1773 |
| X06233 | mRNA for calcium-binding protein In macrophages (MRP-14) | 7 | 11 | 3007 |
| D85181 | mRNA for fungal sterol-C5-desaturase homolog | 6 | 11 | 3571 |
| M31627 | X box binding protein-1 (XBP-1) | 5 | 10 | 12151 |

TABLE 2

Cy3 versus Cy5 ratio for a set of genes that are previously shown to express at relative constant level (2)

| Accession # | Description | Before extensive washing (Cy3/Cy5) | After extensive washing (Cy3/Cy5) |
|---|---|---|---|
| X06323 | MRL3 mRNA for ribosomal protein L3 homologue | 3.31 | 5.22 |
| AF006043 | 3-phosphoglycerate dehydrogenase | 3.81 | 4.8 |
| M37400 | Cytosolic aspartate aminotransferase | 3.03 | 3.66 |
| D30655 | mRNA for eukaryotic initiation factor 4A11 | 4.17 | 3.48 |

TABLE 2-continued

Cy3 versus Cy5 ratio for a set of genes that are previously shown to express at relative constant level (2)

| Accession # | Description | Before extensive washing (Cy3/Cy5) | After extensive washing (Cy3/Cy5) |
|---|---|---|---|
| J04208 | inosine-5'-monophosphate dehydrogenase (IMP) | 1.13 | 2.15 |
| M17885 | Acidic ribosomal phosphoprotein PO | 2.74 | 2.09 |
| X54326 | mRNA for glutaminyl-tRNA synthetase | 1.17 | 2.01 |
| J04973 | Cytochrome bc-1 complex core protein II | 0.98 | 1.6 |
| D13900 | mitochondrial short-chain enoyl-CoA hydratase | 0.91 | 1.52 |
| Z1531 | mRNA for elongation factor 1-gamma | 0.76 | 0.89 |
| D78361 | mRNA for ornithine decarboxylase antizyme | 0.51 | 0.82 |
| U13261 | eIF-2 associated p67 homolog | 0.41 | 0.82 |
| X15183 | mRNA for 90-kDa heat-shock protein | 0.8 | 0.75 |
| M36340 | ADP-ribosylation factor 1 (ARF1) | 0.5 | 0.66 |
| X91257 | mRNA for seryl-tRNA synthetase | 0.75 | 0.52 |
| AF047470 | Malate dehydrogenase precursor (MDH) mRNA | 0.41 | 0.51 |
| D13748 | mRNA for eukaryotic initiation factor 4A1 | 0.33 | 0.43 |
| L36151 | Phosphatidylinosito14-kinase | 0.26 | 0.38 |
| X04297 | mRNA for Na,K-ATPase alpha-subunit | 0.27 | 0.34 |
| X79535 | mRNA for beta tubulin, clone nuk_278 | 0.18 | 0.28 |
| J04173 | Phosphoglycerate mutase (PGAM-B) | 0.14 | 0.23 |

TABLE 3

Real-time quantitative RT-PCR analysis of a few selected genes[a].

| | GA733-2 | Osteopontin | KOC | Prostasin | Creatin Kinase B | CEA | RGS |
|---|---|---|---|---|---|---|---|
| Normal ovarian cells | | | | | | | |
| HOSE695 | 4 | 21 | 5 | 28 | 0.4 | 5 | 32 |
| HOSE697 | 1 | 1 | 2 | 4 | 0.4 | 3 | 18 |
| HOSE713 | 1 | 20 | 7 | 5 | 1 | 16 | 25 |
| HOSE726 | 1 | 1 | 1 | 1 | 1 | 1 | 1 |
| Average (HOSE) | 2 | 11 | 4 | 9 | 1 | 6 | 19 |
| Ovarian cancer cell lines | | | | | | | |
| OVCA3 | 419 | 6 | 4 | 61 | 393 | 1 | 4 |
| OVCA432 | 136 | 0 | 0 | 17 | 8 | 0 | 1 |
| OVAC433 | 2048 | 0 | 52 | 57 | 12 | 1 | 4 |
| OVCA633 | 2917 | 13777 | 3 | 228 | 4 | 15 | 27 |
| SKOV3 | 2856 | 265 | 10 | 2 | 31 | 6 | 13 |
| ALST | 3875 | 6081 | 78 | 10 | 1 | 2 | 5 |
| Average (OVCA) | 2042 | 3355 | 24 | 62 | 75 | 4 | 9 |
| OVCA/HOSE (average) | 1361 | 310 | 6 | 7 | 103 | 1 | 0.5 |

[a]Each gene was analyzed using an identical panel of 10 cDNA samples that comprised of 4 normal ovarian surface epithelial cells and 6 ovarian cancer cell lines. The expression of each gene for each cDNA sample was normalized against cyclosporin. Duplicated reactions were performed for each of the genes and similar results were obtained.

Example 2
Differentially Expressed Genes

A. Choice of Samples and the Identification of Differentially Expressed Genes

We compared the expression of 2400 genes between primary human ovarian surface epithelial (HOSE) cells and ovarian cancer (OVCA) cells using the MICROMAX™ CDNA microarray system (NEN Life Science Products, Boston, Mass., USA). Three primary HOSE cells from different individuals were pooled together as a normal sample. The use of pooled normal samples has two advantages—(1) fluctuations in gene expression among normal HOSE cells due to the individual difference in age or physiological states may be minimized, and (2) a sufficient amount of RNA for direct labelling can be obtained from the precious primary cell cultures. Similarly, three different cancer cell lines were pooled together as an ovarian cancer sample for the analysis.

47 genes over-expressed (Table 4 and Table 5), and 58 genes down-regulated in ovarian cancer cells (Table 6) were identified from a single microarry experiment. However, the list of genes described here is different from two similar studies reported previously (Schummer, et al., *Gene* 238:375 (1999), Wang, et al., *Gene* 229:101, (1999)). Only a few differentially expressed genes were shared by these studies. The differences in the list of differentially expressed genes may be due to the use of different samples in the analysis. We compared the gene expression of primary normal ovarian surface epithelial cells and ovarian cancer cell lines. In one of the previous studies, gene expression of normal ovary was compared with tumor tissues, while gene expression of low passage ovarian surface epithelial cells were compared with tumor tissues in another study. Apparently, the choice of samples for analysis would account for the different set of genes identified.

B. Background Hybridization Signal and the Identification of Weakly Expressed Genes Gene expression from OVCA samples was detected as a Cy3 signal while gene expression from HOSE samples was detected as Cy5 signal. After completion of the recommended procedures, significant background signal was still observed in the Cy3 signal that derived from OVCA sample. A series of additional, stringent post-hybridization washes reduced the background signal. While the Cy3 to Cy5 ratios for most of the genes increased slightly after stringent post-hybridization washes, the ratios, for some genes increased significantly. More importantly, after the stringent post-hybridization washes, we were able to detect the weakly expressed genes that are differentially over-expressed in ovarian cancer cells (Table 5).

C. Genes Over-expressed in Ovarian Cancer Cells

From the list of over-expressed genes, several putative mechanisms may be involved in the pathogenesis of ovarian cancer—(1) inactivation of a tumor suppressor, (2) altered expression of transcription factors, (3) overexpression of oncogenes, (4) overexpression of glycosylphosphatidylinositol (GPI) anchor associated proteins, and (5) altered cell cycle control. According to this list of genes, VBP1 interacts with the product of the von Hippel-Lindau gene and is expected to participate in pathways by inactivation of this tumor suppressor gene. RNA binding proteins, Koc and hnRNP D, may assume a role in the regulation of tumor cell proliferation by interfering with transcriptional and/or post-transcriptional processes of tumor suppressor genes. However, the precise role of these RNA binding proteins in human tumor cells remains to be elucidated. ATF3 and XBP-1 are transcription factors which may play an important role in the regulation of gene expression by cAMP-dependent intracellular signaling pathways and be essential for hepatocyte growth respectively. Also related to gene transcription, HMG-I protein has been implicated as a potential marker for thyroid carcinoma. p18 and E16 are two oncogenes that have been found to be over-expressed in acute leukemia cells and various human cancers respectively. The glycosylphosphatidylinositol (GPI) anchor, potentially capable of generating a number of second messengers, such as diacylglycerol, phosphatidic acid, and inositol phosphate glycan, has been postulated to be involved in signal transduction in various cell types, including T-cells. Genes encoding GPI anchored proteins. (GPI-H, B61 and CD24) were found to be over-expressed in ovarian cancer cells. Myt1 activity is temporally regulated during the cell cycle and is suggested to play a role in mitotic control. CD24, a GPI anchored protein, is also involved in cell cycle control.

The differential expression of five interesting genes, GA733-2, osteopontin, koc, prostasin, and creatine kinase B, has previously been confirmed by real-time RT-PCR. All these genes are either surface antigens or secreted proteins, which may be potential serum markers. In fact, we have found that prostasin is significantly higher in the plasma of an ovarian cancer patient. GA733-2 is known as epithelial cell surface antigen (EPG) or adenocarcinoma-associated antigen (KSA). These proteins may function as growth factor receptors. Osteopontin is an acidic phosphorylated glycoprotein of about 40 Kd which is abundant in the mineral matrix of bones and possibly functions as a cell attachment factor involved in tumor invasion and metastasis. Prostasin is a serine proteinase expressed in prostate and prostate carcinoma. Creatine kinase has been shown to be at an elevated level in the blood of patients with renal cell carcinoma or small lung carcinoma.

D. Genes Down-regulated in Ovarian Cancer Cells

More than 50 genes down-regulated in ovarian cancer cells were identified in this study. In this list of genes (Table 6), SPARC/osteonectin has been previously identified as a down-regulated gene. SPARC is an extracellular matrix (ECM) protein with tumor-suppressing activity in human ovarian epithelial cells (Mok, et al., Oncogene 12:1895, (1996)). Other ECM or ECM related proteins such as fibronectin, tenascin, OB-cadherin-1, HXB, matrix metalloproteinase, and ICAM-1 were also found to be down-regulated. Tenascin has been suggested to be a prognostic marker for colon cancer. Patients with more tenascin expression have better long-term survival than patients with no or weak expression.

Several other genes involved in responding to growth factors or mitogens were also down-regulated. These genes were Shps-1, phosphorylase-kinase, phosphoinositide 3-kinase, NDP kinase, ZIP-kinase, signal transducing guanine nucleotide-binding regulatory protein, IGFBP2, TGF-beta, and TNFα receptor. SHPS-1, a novel glycoprotein, binds the Sh2-domain-containing protein tyrosine phosphatase SHP-2 in response to mitogens and cell adhesion. Suppression of SHPS-1 expression by v-Src via the Ras-MAP kinase pathway has been shown to promote the oncogenic growth of cells. NDP kinase gene located on chromosome 17q has been proposed as a metastasis suppressor gene in a variety of tumor types. ZIP kinase is a novel serine/threonine kinase and has been shown to mediate apoptosis through its catalytic activities. Previous work suggests that the TGF-beta receptor complex and its downstream signaling intermediates constitute a tumor suppressor pathway. The stabilization of TNF-alpha receptors on the surface of human colon carcinoma cells is necessary for TNFα induced cell death. Besides these two major groups of genes, other genes encoding proteases and complement C1 components were also down-regulated. Some of these down-regulated genes, such as testican and osteoblast specific factor 2, have not yet been associated with carcinogenesis.

TABLE 4

| Accession # | Description | (OVCA/HOSE) | OVCA signal intensity |
|---|---|---|---|
| M33011 | carcinoma-associated antigen GA733-2 | 444 | 1249 |
| 704765 | Osteopontin | 184 | 11851 |
| L41351 | Prostasin | 170 | 3172 |
| L19783 | GPI-H | 88 | 916 |
| U96759 | Von Hippel-Lindau binding protein (VBP-1) | 59 | 1377 |
| M57730 | B61 | 49 | 5514 |
| L33930 | CD24 signal transducer and 3' region | 47 | 26722 |
| D55672 | hnRNP D | 44 | 950 |
| U97188 | Putative RNA binding protein KOC | 38 | 3599 |
| L19871 | ATF3 | 37 | 3507 |
| 704991 | p18 | 34 | 9914 |
| D00762 | proteasome subunit HC8 | 29 | 4703 |
| U17989 | Nuclear autoantigen GS2NA | 28 | 721 |
| U43148 | Patched homolog (PTC) | 28 | 4155 |
| AF010312 | Pig7 (PIG7) | 23 | 17379 |

TABLE 4-continued

| Accession # | Description | (OVCA/HOSE) | OVCA signal intensity |
|---|---|---|---|
| M80244 | E16 | 21 | 4180 |
| X99802 | ZYG homologue | 21 | 2086 |
| U05598 | Dihydrodiol dehydrogenase | 18 | 21595 |
| L47647 | Creatine kinase B. | 18 | 787 |
| M55284 | Protein kinase C -L (PRKCL) | 16 | 863 |
| X15722 | glutathione reductase | 14 | 794 |
| 554005 | Thymosin beta-10 | 13 | 1476 |
| AB006965 | Dnmlp/Vpslp-like protein | 13 | 4183 |
| M83653 | Cytoplasmic phosphotyrosyl protein phosphatase | 13 | 2156 |
| X12597 | high mobility group-1 protein (HMG-1) | 12 | 2785 |
| M18112 | poly(ADP-ribose) polymerise | 12 | 9277 |
| U56816 | Kinase Mytl (Mytl) | 11 | 1773 |
| X06233 | calcium-binding protein in macrophages (MRP-14) | 11 | 3007 |
| D85181 | fungal sterol-C5-desaturase homolog | 11 | 3571 |
| M31627 | Xbox binding protein-1 (XBP-1) | 10 | 12151 |

TABLE 5

Weakly expressed genes identified after stringent washes.

| AF005654 | Actin-binding double-zinc-finger protein (abLIM). | 18770 | 751 |
|---|---|---|---|
| L10844 | Cellular growth-regulating protein. | 33 | 725 |
| M88163 | Global transcription activator homologous sequence. | 18 | 642 |
| U02882 | Rolipram-sensitive 3', 5'-cyclic AMP phosphodiesterase. | 27 | 636 |
| X12517 | U1 small nuclear RNP-specific C protein. | 112 | 550 |
| D29833 | Salivary proline rich peptide P-B. | 10 | 492 |
| AF020918 | Glutathione transferase GSTA4 | 47 | 475 |
| J05262. | Farnesyl pyrophosphate synthetase | 95 | 469 |
| L08424 | Achaete scute homologous protein (ASH1). | 57 | 457 |
| M84526. | Adipsin/complement factor D | 65 | 441 |
| U35113 | Metastasis-associated mtal. | 13 | 367 |
| D28468 | DNA-binding protein TAXREB302. | 268 | 357 |
| AF012126 | Zinc finger protein (ZNF198). | 15 | 342 |
| AB000714 | RVP1. | 11 | 314 |
| AF029750 | Tapasin(NGS-17). | 118 | 305 |
| X60489 | Elongation factor-1-beta. | 10 | 282 |
| L36645 | Receptor protein-tyrosine kinase (HEK8). | 71 | 273 |

TABLE 6

List of genes down-regulated in ovarian cancer cells more than 10-fold.

| Accession # | Description | (HOSE/OVCA) | HOSE signal |
|---|---|---|---|
| D45421 | phosphodiesterase I alpha | ∞ | 667 |
| M35410 | Insulin-like growth factor binding protein 2 (IGFBP2) | ∞ | 1517 |
| X81334 | collagenase-3 protein | ∞ | 5146 |
| D13665 | osteoblast specific factor 2 (OSF-2p1) | ∞ | 24300 |
| J03040 | SPARC/osteonectin | ∞ | 28711 |
| D86043 | SHPS-1 | 681 | 9450 |
| U89942 | Lysyl oxidase-related protein (WS9-14) | 454 | 25055 |
| M59807 | NK4 | 118 | 22438 |
| Z74616 | Prepro-alpha2(I) collagen | 101 | 2281 |
| Z74615 | Prepro-alpha1(I) collagen | 81 | 24323 |
| X06596 | Complement component C1s | 76 | 22672 |
| M95787 | 22kDa smooth muscle protein (SM22) | 71 | 31581 |
| X06256 | Fibronectin receptor alpha subunit | 66 | 27901 |
| M36981 | Putative NDP kinase (nm23 H2S) | 60 | 15411 |
| AJ001838 | Maleylacetoacetate isomerase | 59 | 304 |
| X56160 | Tenascin | 42 | 36062 |
| D21254 | OB-cadherin-1 | 40 | 20621 |
| Y07921 | Serine protease | 37 | 2247 |
| Y10032 | Putative serine/threonine protein kinase | 36 | 8510 |
| X04526 | Beta-subunit signal transducing proteins Gs/Gi (beta-G) | 36 | 13321 |
| L31409 | Creatine transporter | 35 | 8677 |
| X04701 | Complement component C1r | 33 | 10299 |
| X13839 | Vascular smooth muscle alpha-actin | 32 | 27311 |
| X84908 | Phosphorylase-kinase, beta subunit | 30 | 11341 |
| L14595 | Alanine/serine/cysteine/threonine transporter (ASCT1) | 27 | 2234 |
| M97796 | Helix-loop-helix protein (Id-2) | 25 | 3187 |
| X04741 | Protein gene product (PGP) 9.5 | 25 | 13138 |
| Y10055 | Phosphoinositide 3-kinase | 23 | 614 |
| X83535 | Membrane-type matrix metalloproteinase | 20 | 6464 |
| U69546 | RNA binding protein Etr-3 | 18 | 2714 |
| U16268 | AMP deaminase isoform L, alternatively spliced (AMPD2) mRNA, exons 113, 2 and 3. | 18 | 3512 |
| S59749 | SE10 antigen | 18 | 1249 |
| U03057 | Actin bundling protein (HSN) | 17 | 9285 |
| J02854 | 20-kDa myosin light chain (MLC-2) | 16 | 8323 |
| X16940 | Enteric smooth muscle gamma-actin | 16 | 18776 |
| X13223 | N-acetylglucosamide-(beta 1–4)-galactosyltransferase | 16 | 3357 |
| M69181 | Nonmuscle myosin heavy chain-B (MYH10) | 16 | 11126 |
| X06990 | ICAM-1 | 16 | 25605 |
| M13656 | Plasma protease (C1) inhibitor | 15 | 1091 |
| X73608 | Testican | 15 | 2977 |
| M96803 | General beta-spectrin (SPTBNI) | 15 | 13359 |
| D00632 | Glutathione peroxidase | 15 | 4951 |
| X03445 | Nuclear envelope protein lamin C precursor | 13 | 17451 |
| L06419 | Lysyl hydroxylase (PLOD) | 13 | 9288 |
| M12125 | Fibroblast muscle-type tropomyosm | 12 | 34379 |

TABLE 6-continued

List of genes down-regulated in ovarian cancer cells more than 10-fold.

| Accession # | Description | (HOSE/OVCA) | HOSE signal |
|---|---|---|---|
| S45630 | Alpha B-crystallin, Rosenthal fiber component. | 12 | 1536 |
| AB005298 | BAI 2 | 11 | 3839 |
| L77864 | Stat-like protein (Fe65) | 11 | 1914 |
| AB007144 | ZIP-kinase | 11 | 4277 |
| M16538 | Signal-transducing guanine nucleotide- binding regulatory (G) protein beta subunit | 11 | 2793 |
| L35545 | Endothelial cell protein C/APC receptor (EPCR) | 11 | 1002 |
| M75161 | Granulin | 11 | 13289 |
| X69910 | p63 | 11 | 16460 |
| D12686 | eTF-4 gamma | 11 | 21555 |
| L07594 | Transforming growth factor-beta type III receptor (TGF-beta) | 11 | 672 |
| M33294 | Tumor necrosis factor receptor | 10 | 6592 |
| U18121 | 136-kDa double-stranded RNA binding protein p136 (K88dsRBP) | 10 | 1619 |
| M55618 | Hexabrachion(HXLB) | 10 | 3866 |

Example 3
Prostasin as a Serum Marker for Ovarian Cancer
I. Materials and Methods
Biological Specimens Ovarian tissue and cells were freshly collected from women undergoing surgery at the Brigham and Women's Hospital for diagnosis of primary ovarian cancer or from control subjects having a hysterectomy and ophorectomy for benign disease. Cultures of normal ovarian surface epithelial (HOSE) cells were established by scraping the surface of the ovary and growing recovered cells in a mixture of medium 199 and MCDB 105 medium supplemented with 10% fetal calf serum. The following seven normal HOSE cells were used: HOSE17, HOSE636, HOSE642, HOSE697, HOSE713, HOSE726 and HOSE730. Ovarian cell lines were established by recovery from ascites fluid or explanted from solid tumors. The following ten ovarian cancer cell lines were used: OVCA3, OVCA420, OVCA429, OVCA432, OVCA433, OVCA633, CAOV3, DOV13, ALST and SKOV3.

Serum specimens from women with ovarian cancer, other gynecologic cancers and benign gynecologic disorders requiring hysterectomy and from non-diseased normal women were obtained from discarded specimens, from discarded specimens that were archived during the period from 1983 through 1988 or from specimens collected under more recent protocols since 1996. The archived samples were collected from several studies assessing the performance of CA 125 in a variety of diagnostic circumstances, including gynecologically normal subjects as well as subjects having exploratory surgery for pelvic masses that proved to be ovarian, cervical or endometrial cancer for a benign disease such as a fibroid tumor. The archived specimens were stored at −70° C. However, thawing was known to have occurred once for some of the archived specimens. More recent specimens were obtained within the past five years and were stored at −70° C. without any incident of thawing. In both specimen banks, serum from case patients with ovarian cancer and serum from control patients were collected concurrently.

Microarray Probe and Hybridization

The MICROMAX™ Human cDNA Microarray System I(NEN Life Science Products, Inc. Boston, Mass.) was used in this study. Biotin-labeled cDNA was generated from 3 micrograms of total RNA that was pooled from HOSE17, HOSE636 and HOSE642 cells. Dinitrophenyl-labelled cDNA was generated from 3 micrograms of total RNA that was pooled from ovarian cancer cell lines OVCA420, OVCA433, and SKOV3. Before the cDNA reaction, 5 ng of Arabidopsis control RNA were added to each batch of the RNA samples for the normalization of hybridization signals. The biotin-labelled cDNA and the dinitrophenyl-labelled cDNA were mixed, dried and resuspended in 20 microliters of hybridization buffer 5×standard saline citrate (SSC), 0.1% sodium dodecyl sulfate (SDS) and salmon sperm DNA at 0.1 mg/ml (1×SSC =0.15 M NaCl, 0.15 M sodium citrate, pH 7). This mixture was added to the cDNA microarray and was covered with a coverslip. Hybridization was carried out overnight at 65° C. inside a hybridization cassette.

After hybridization, the microarray was washed with 30 ml of 0.5×SSC-0.01% SDS, with 30 ml of 0.06×SSC-0.01% SDS and then with 30 ml of 0.06×SSC alone. The hybridization signal from biotin-labelled cDNA was amplified with streptavidin-horseradish peroxidase and fluorescent dye, Cy5-tyramide. The hybridization signal from the dinitrophenyl-labelled cDNA was amplified with anti-dinitrophenyl-horseradish peroxidase and another fluorescent dye, Cy3-tyramide. After signal amplification and post-hybridization wash in TNT buffer (i.e., 0.1 M Tris-HCl (pH 7.5)-0.15 M NaCl-0.15% Tween20), the microarray was air-dried and signal amplification was detected with a laser scanner.

Laser detection of the Cy3 signal (derived from ovarian cancer cells) and the Cy5 signal (derived from HOSE cells) on the microarray was acquired with a confocal laser reader. Separate scans were taken for each fluor at a pixel size of 10 micrometers. cDNA derived from the added Arabidopsis RNA hybridized to 12 specific spots on the microarray, which were composed of DNA sequences obtained from four different Arabidopsis expressed sequence tags in triplicate. Cy3 and Cy5 signals from these 12 spots should theoretically be equal and were used to normalize the different efficiencies in labeling and detection with the two fluors. The fluorescence signal intensity and the ratio of the signals from Cy3 and Cy5 for each of the 2400 cDNAs were analyzed by the software Imagene 3.0 (Biodiscovery Inc., Los Angeles, Calif.).

Real-Time Quantitative Reverse Transcription-Polymerase Chain Reaction

Real-time reverse transcription-polymerase chain reaction (RT-PCR) was performed in duplicate by using primer sets specific for the overexpressed gene encoding the secretory protein prostasin (forward primer=5'-ACTTGAGCCACTCCTTCCTTCAG-3' (SEQ ID NO:3); reverse primer=5'-CTGATGGTCCCAAAAAGCACAC-3' (SEQ ID NO:4)) and a housekeeping gene, GADPH. RNA was first extracted from normal ovarian epithelial cell cultures (HOSE697, HOSE713, HOSE726, and HOSE730) and from 10 ovarian carcinoma cell lines (OVCA3, OVCA420, OVCA429, OVCA432, OVCA433, OVCA633, CAOV3, DOV13, SKOV3, and ALST). cDNA was generated from 1 microgram of total RNA using the TaqMan RT reagents containing 1×TaqMan reverse transcriptase buffer, 5.5 mM $MgCl_2$, all four deoxyribonucleoside triphosphates (each at 500 $\mu$M), 2.5 $\mu$M random hexamers, MultiScribe reverse transcriptase at 1.25 U/$\mu$l, and RNasin at 0.4 U/$\mu$l in 100 $\mu$l. The reaction was incubated at 25° C. for ten minutes at 48° C. for thirty minutes and finally at 95° C. for five minutes. A total of one microgram of cDNA was used in 20 $\mu$l PCR mixture containing 1×SYBR PCR buffer, 3 mM $MgCl_2$, all for deoxyribonucleoside triphosphates (each at 0.8 mM) and AmpliTaq Gold. The cDNAs were then amplified by denaturation for ten minutes at 95° C., followed by 40 PCR cycles of denaturation at 95° C. for 15 seconds and annealing-extension at 60° C. for one minute. The changes in fluorescence of the SYBR Green I dye in every cycle were monitored by ABI 5700 system software and the threshhold cycle, which represents the PCR cycle at which an increase in reporter fluorescence above a baseline signal can first be detected for each reaction, was calculated. The relative amount of PCR products generated from each primer set was determined on the basis of the threshhold cycle ($C_T$) value. GAPDH was used to normalize the quantity of RNA used. Its $C_T$ value was then subtracted from each target gene to obtain a $\Delta C_T$ value. The difference between the $\Delta C_T$ values of the samples for each gene target and the $\Delta C_T$ value of a calibrator which served as a physiologic reference was determined. For confirmation of the specificity of the PCR, PCR products were subjected to electrophoresis on a 1.2% agrose gel. A single PCR product with the expected size should be observed in samples that express the gene of interest.

Immunohistochemical Localization of Prostasin

Immunostaining with anti-prostasin antibody was performed on sections prepared from two normal ovaries, from two serous borderline ovarian tumors, and from two grade 1, two grade 2, and two grade 3 serous ovarian adenocarcinomas. This rapid polyclonal antibody, also used in the serum assay was prepared from prostasin purified from human seminal fluid as described previously (Yu, et al., *J. Biol. Chem.* 269:18843–18848 (1994)). Tissues were fixed in 4% paraformaldehyde and embedded in paraffin. Sections (5 $\mu$m) were cut, mounted on microscopic slides and incubated at 50° C. overnight. They were then transferred to Tris-buffered saline (TBS) and quenched in 0.2% $H_2O_2$ for 20 minutes. After quenching, the sections were washed in TBS for 20 minutes, incubated with normal horse serum for 20 minutes, and then incubated with anti-prostasin polyclonal antibody (diluted 1:400) at room temperature for one hour. The slides were then washed in TBS for 10 minutes, incubated with diluted biotinylated secondary horse anti-rabbit antibody solution for 30 minutes, washed again in TBS for 10 minutes, incubated with avidin-biotin complex reagent for 30 minutes and washed in TBS for 10 minutes. Stain development was performed for 5 minutes using a diaminobenzidine kit. Finally, the sections were washed in water for 10 minutes. They were then counterstained with hemanoxylin, dehydrated with an ascending series of alcohol solutions, cleared in xylene and mounted. The specificity of the staining was confirmed by using preimmunization rabbit serum and by preabsorbing the antibody with the purified peptide (60 mg/ml) or prostasin for 2 hours at 37° C. before applying the adsorbed antiserum to the sections.

Measurement of Prostasin and CA 125 in Sera

Sera were available from a total of 201 subjects (64 case patients with ovarian cancer and 137 control subjects, including 34 with other gynecologic cancers, 42 with benign gynecologic diseases, and 71 with no known gynecologic diseases). In all of the case patients and in the 68 control subjects who had surgery, preoperative specimens were available. Serum levels of immunoreactive human prostasin were determined by the enzyme-linked immunosorbent assay (ELICA) prepared with the previously described antibody to human prostasin. Microtiter plates (96 well) were coated with anti-prostasin immunoglobulin G (IgG) (1 $\mu$g/ml, 100 $\mu$l per well) overnight at 4° C. Purified prostasin standards or samples were added to individual wells in a total volume of 100 $\mu$l of phosphate-buffered saline containing 0.05% Tween 20 and 0.5% gelatin (dilution buffer) and incubated at 37° C. for 90 minutes. Biotin labeled anti-human prostasin IgG was added to each well at a concentration of 1 $\mu$g/ml in a total of 100 $\mu$l and incubated at 37° C. for 60 minutes. Peroxidase-avidin at a concentration of 1 $\mu$l/ml in a total volume of 100 $\mu$l was added and incubated at 37° C. for 30 minutes. The color reaction was performed by adding to each well 100 $\mu$l of freshly prepared substrate solution and 0.03% $H_2O_2$ in 0.1 M sodium citrate (pH 4.3) and incubating the mixture at room temperature for 30 minutes. The plates were read at 405 nm with a plate reader.

For 37 case patients with ovarian cancers and for 100 control subjects (about 70% of all subjects) a CA 125 level had been determined previously (from the same specimens) and was available for comparison. These measurements had been performed with the original CA 125 radioimmunoassay from Centocor and the assays were not repeated for this study.

Statistical Analysis

Univariate comparisons for quantitative variables between normal and cancer cell lines or between case and control sera were made using Student's t test. For analysis of serum levels, adjustment for potential confounding variables such as the subject's age, year of collection and whether the specimen had undergone freezing and thawing was carried out using general linear modeling. Logistic regression analysis was used to determine the statistical significance of both prostasin and CA 125 as a predictor of case status. Paired Student's t test was used to compare the change in postoperative prostasin levels from preoperative levels. Pearson correlation coefficients were calculated between CA 125 and prostasin. Because the distributions of prostasin and CA 125 were skewed positively, log-transformed values were used in statistical tests. Analyses with a P value of 0.05 or less were considered to be statistically significant. All statistical tests were two sided and all confidence intervals are 95%.

II. Results

Microarray analysis of pooled RNA isolated from three normal HOSE cell lines and from three ovarian cancer cell lines was performed. Thirty genes with Cy3/Cy5 signal ratios ranging from 5 to 444 were identified, suggesting that these genes were overexpressed in ovarian cancer cells compared with normal HOSE cells. Among them, both prostasin and osteopontin encode secretory proteins which may be potential serum markers. Another gene, creatine kinase B has been shown to produce a serum marker associated with renal carcinoma and lung cancer. Prostasin was selected for further study because this gene had an available antibody assay.

To evaluate the differential expression of prostasin in individual normal and malignant ovarian epithelial cell lines derived from normal and neoplastic ovaries, we performed quantitative PCR analysis on four normal HOSE cultures and on ten ovarian cancer cell lines. The relative prostasin gene expression ranged from 120.3-fold to 410.1-fold greater for seven of the ten ovarian cancer cell lines compared with that for HOSE 697 cells but was only marginally greater for three other ovarian cell lines. Overall, there was a highly statistically significant difference between expression for the four normal cell lines compared to the ten ovarian cancer cell lines P<0.001.

For further validation of the expression of prostasin in actual tumor tissue, sections from two normal ovaries, from two serous borderline ovarian tumors and from two grade 1, two grade 2 and two grade 3 serous ovarian cystadenocarcinomas were immunostained with an anti-prostasin polyclonal antibody. Stronger cytoplasmic staining was detected in cancer cells than in normal HOSE cells, suggesting that prostasin is overexpressed by the ovarian cancer cells. Prostasin was, however, also detected in normal ovarian tissue by immunostaining. We next examined prostasin levels detected by ELISA in sera from case patients and control subjects. The mean prostasin level for all of the case patients was 13.7 μg/ml compared with 7.5 μg/ml in all of the control subjects. Based on log-transformed values, this difference was statistically significant (P<0.001) and persisted after adjustment for the subject's age, year of collection, and quality of specimen (possible freeze-thaw damage). Among case patients, there was considerable variability by stage; however, notably women with stage II disease had the highest levels of prostasin, suggesting that prostasin may be of use for early-stage detection. It also appeared that women with mucinous-type ovarian tumors had lower levels of prostasin than women with ovarian tumors of other epithelial types. Among control subjects, there was a statistically significant tendency for the archived specimens to have lower prostasin levels than the current specimens (P<0.001), but there was no evidence for an effect of age or diagnostic category (i.e., normal tissue, benign gynecologic disease, or other gynecologic cancer). In addition, 60.5% of the archived case specimens and 66.2% of the control specimens had been in the freezer in which freezing and thawing had occurred. There was no evidence of a tendency for these samples to have lower prostasin levels.

In sixteen women with nonmucinous epithelial ovarian cancers, preoperative and postoperative specimens were available for comparison. For fourteen of these women, a decreased prostasin level was observed after surgery, and, in the entire group of sixteen, postoperative P levels were statistically lower when compared with preoperative levels using a pair T test on the log-transformed values (P=0.004).

A bivariate plot of prostasin versus CA 125 performed for the 37 case patients with nonmucinous ovarian cancers and for the 100 control subjects who had both measurements available failed to show a statistically significant correlation. This lack of correlation suggests that the two markers may provide complementary information. The combined markers had a sensitivity of 34/37 (92%) and a specificity of 94/100 (94%). In contrast, the sensitivity of CA 125 alone at the same specificity was 24/37 (64.9%) and the sensitivity of prostasin alone at the same specificity was 19/37 (51.4%).

III. Discussion

The present study demonstrates prostasin's potential as a biomarker through real-time PCR in cancer and normal epithelial cell lines and by differential staining in cancer tissue compared with normal tissue. Higher levels of serum prostasin were found to be present in case patients with ovarian cancer when compared to control subjects and a declining level of prostasin was observed after surgery for ovarian cancer. Results also suggest that assays with prostasin may be combined with those for other markers such as CA 125 to improve the reliability of procedures for the detection of ovarian cancer.

What is claimed is:

1. A method of determining whether a woman is at increased risk of having ovarian cancer, comprising:
   (a) obtaining a test sample of plasma or serum from said woman;
   (b) determining the concentration of prostasin in said test sample;
   (c) comparing the results of the determination of step (b) with results obtained using a control sample; and
   (d) concluding that said woman is at increased risk of having ovarian cancer if the concentration of prostasin in said test sample is significantly higher than the concentration in said control sample.

2. The method of claim 1, wherein the concentration of prostasin in said test sample and said control sample is determined by ELISA.

3. A method of determining whether a woman is at increased risk of having ovarian cancer, comprising:
   (a) obtaining a test sample of plasma or serum from said woman;
   (b) determining the concentration of prostasin in said test sample; and
   (c) concluding that said woman is at increased risk of having ovarian cancer if the concentration of prostasin is greater than 10 µg/ml.

4. The method of claim 3, wherein a conclusion is drawn that said woman has or is likely to develop ovarian cancer if the concentration of prostasin is greater than 12 µg/ml.

5. The method of claim 3, wherein said prostasin concentration is determined by means of an ELISA assay.

6. The method of any one of claims 1–4, further comprising assaying said plasma or serum sample for CA 125.

7. A method of determining whether a woman is at increased risk of having ovarian cancer, comprising:
   (a) obtaining a test sample of ovarian cells from said woman;
   (b) determining the amount of prostasin protein in said test sample;
   (c) comparing the results of the determination of step (b) with results obtained using a control sample; and
   (d) concluding that said woman is at increased risk of having ovarian cancer if the amount of prostasin in said test sample is significantly higher than the amount in said control sample.

8. The method of claim 7, wherein said amount of prostasin protein is determined by means of an ELISA assay.

* * * * *

UNITED STATES PATENT AND TRADEMARK OFFICE
CERTIFICATE OF CORRECTION

PATENT NO.         : 6,846,642 B2                                    Page 1 of 1
APPLICATION NO.    : 09/948094
DATED              : January 25, 2005
INVENTOR(S)        : Mok et al.

It is certified that error appears in the above-identified patent and that said Letters Patent is hereby corrected as shown below:

In column 1, immediately prior to line 10 which has the heading, "FIELD OF THE INVENTION," the following text is inserted:

-- STATEMENT OF GOVERNMENT FUNDING

This invention was made with Government support under Grant No. DAMD17-99-1-9563 awarded by the U.S. Department of the Army. The U.S. Government has certain rights in this invention. --

Signed and Sealed this

Fifteenth Day of January, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 1834
<212> TYPE: DNA
<213> ORGANISM: Homo sapiens
<220> FEATURE:
<221> NAME/KEY: CDS
<222> LOCATION: (229)..(1260)

<400> SEQUENCE: 1

```
agacggtgct ggtgactcgt ccacactgct cgcttcggat actccaggcg tctcccgttg      60
cggccgctcc ctgccttaga ggccagcctt ggacacttgc tgcccctttc cagcccggat     120
tctgggatcc ttccctctga gccaacatct gggtcctgcc ttcgacacca ccccaaggct     180
tcctaccttg cgtgcctgga gtctgcccca ggggcccttg tcctggcc atg gcc cag     237
                                                      Met Ala Gln
                                                        1 aag ggg gtc ctg ggg cct ggg cag ctg ggg gct gtg gcc att ctg ctc       285
Lys Gly Val Leu Gly Pro Gly Gln Leu Gly Ala Val Ala Ile Leu Leu
  5                  10                  15 tat ctt gga tta ctc cgg tcg ggg aca gga gcg gaa ggg gca gaa gct       333
Tyr Leu Gly Leu Leu Arg Ser Gly Thr Gly Ala Glu Gly Ala Glu Ala
 20                  25                  30                  35 ccc tgc ggt gtg gcc ccc caa gca cgc atc aca ggt ggc agc agt gca       381
Pro Cys Gly Val Ala Pro Gln Ala Arg Ile Thr Gly Gly Ser Ser Ala
                 40                  45                  50 gtc gcc ggt cag tgg ccc tgg cag gtc agc atc acc tat gaa ggc gtc       429
Val Ala Gly Gln Trp Pro Trp Gln Val Ser Ile Thr Tyr Glu Gly Val
             55                  60                  65
```

```
cat gtg tgt ggt ggc tct ctc gtg tct gag cag tgg gtg ctg tca gct    477
His Val Cys Gly Gly Ser Leu Val Ser Glu Gln Trp Val Leu Ser Ala
         70                  75                  80 gct cac tgc ttc ccc agc gag cac cac aag gaa gcc tat gag gtc aag    525
Ala His Cys Phe Pro Ser Glu His His Lys Glu Ala Tyr Glu Val Lys
 85                  90                  95 ctg ggg gcc cac cag cta gac tcc tac tcc gag gac gcc aag gtc agc    573
Leu Gly Ala His Gln Leu Asp Ser Tyr Ser Glu Asp Ala Lys Val Ser
100                 105                 110                 115 acc ctg aag gac atc atc ccc cac ccc agc tac ctg cag gag ggc tcc    621
Thr Leu Lys Asp Ile Ile Pro His Pro Ser Tyr Leu Gln Glu Gly Ser
                120                 125                 130 cag ggc gac att gca ctc ctc caa ctc agc aga ccc atc acc ttc tcc    669
Gln Gly Asp Ile Ala Leu Leu Gln Leu Ser Arg Pro Ile Thr Phe Ser
            135                 140                 145 cgc tac atc cgg ccc atc tgc ctc cct gca gcc aac gcc tcc ttc ccc    717
Arg Tyr Ile Arg Pro Ile Cys Leu Pro Ala Ala Asn Ala Ser Phe Pro
        150                 155                 160 aac ggc ctc cac tgc act gtc act ggc tgg ggt cat gtg gcc ccc tca    765
Asn Gly Leu His Cys Thr Val Thr Gly Trp Gly His Val Ala Pro Ser
    165                 170                 175 gtg agc ctc ctg acg ccc aag cca ctg cag caa ctc gag gtg cct ctg    813
Val Ser Leu Leu Thr Pro Lys Pro Leu Gln Gln Leu Glu Val Pro Leu
180                 185                 190                 195 atc agt cgt gag acg tgt aac tgc ctg tac aac atc gac gcc aag cct    861
Ile Ser Arg Glu Thr Cys Asn Cys Leu Tyr Asn Ile Asp Ala Lys Pro
                200                 205                 210 gag gag ccg cac ttt gtc caa gag gac atg gtg tgt gct ggc tat gtg    909
Glu Glu Pro His Phe Val Gln Glu Asp Met Val Cys Ala Gly Tyr Val
            215                 220                 225 gag ggg ggc aag gac gcc tgc cag ggt gac tct ggg ggc cca ctc tcc    957
Glu Gly Gly Lys Asp Ala Cys Gln Gly Asp Ser Gly Gly Pro Leu Ser
        230                 235                 240 tgc cct gtg gag ggt ctc tgg tac ctg acg ggc att gtg agc tgg gga    1005
Cys Pro Val Glu Gly Leu Trp Tyr Leu Thr Gly Ile Val Ser Trp Gly
    245                 250                 255 gat gcc tgt ggg gcc cgc aac agg cct ggt gtg tac act ctg gcc tcc    1053
Asp Ala Cys Gly Ala Arg Asn Arg Pro Gly Val Tyr Thr Leu Ala Ser
260                 265                 270                 275 agc tat gcc tcc tgg atc caa agc aag gtg aca gaa ctc cag cct cgt    1101
Ser Tyr Ala Ser Trp Ile Gln Ser Lys Val Thr Glu Leu Gln Pro Arg
                280                 285                 290 gtg gtg ccc caa acc cag gag tcc cag ccc gac agc aac ctc tgt ggc    1149
Val Val Pro Gln Thr Gln Glu Ser Gln Pro Asp Ser Asn Leu Cys Gly
            295                 300                 305 agc cac ctg gcc ttc agc tct gcc cca gcc cag ggc ttg ctg agg ccc    1197
Ser His Leu Ala Phe Ser Ser Ala Pro Ala Gln Gly Leu Leu Arg Pro
        310                 315                 320 atc ctt ttc ctg cct ctg ggc ctg gct ctg ggc ctc ctc tcc cca tgg    1245
Ile Leu Phe Leu Pro Leu Gly Leu Ala Leu Gly Leu Leu Ser Pro Trp
    325                 330                 335 ctc agc gag cac tga gctggccta cttccaggat ggatgcatca cactcaagga    1300
Leu Ser Glu His
340 caggagcctg gtccttccct gatggccttt ggacccaggg cctgacttga gccactcctt    1360 ccttcaggac tctgcgggag gctgggggccc catcttgatc tttgagccca ttcttctggg    1420 tgtgcttttt gggaccatca ctgagagtca ggagttttac tgcctgtagc aatggccaga    1480
```

| | |
|---|---:|
| gcctctggcc cctcacccac catggaccag cccattggcc gagctcctgg ggagctcctg | 1540 |
| ggacccttgg ctatgaaaat gagccctggc tcccacctgt ttctggaaga ctgctcccgg | 1600 |
| cccgcctgcc cagactgatg agcacatctc tctgccctct ccctgtgttc tgggctgggg | 1660 |
| ccacctttgt gcagcttcga ggacaggaaa ggccccaatc ttgcccactg gccgctgagc | 1720 |
| gcccccgagc cctgactcct ggactccgga ggactgagcc cccaccggaa ctgggctggc | 1780 |
| gcttggatct ggggtgggag taacagggca gaaatgatta aatgtttga gcac | 1834 |

```
<210> SEQ ID NO 2
<211> LENGTH: 343
<212> TYPE: PRT
<213> ORGANISM: Homo sapiens

<400> SEQUENCE: 2
```

Met Ala Gln Lys Gly Val Leu Gly Pro Gly Gln Leu Gly Ala Val Ala
1               5                  10                  15

Ile Leu Leu Tyr Leu Gly Leu Leu Arg Ser Gly Thr Gly Ala Glu Gly
            20                  25                  30

Ala Glu Ala Pro Cys Gly Val Ala Pro Gln Ala Arg Ile Thr Gly Gly
        35                  40                  45

Ser Ser Ala Val Ala Gly Gln Trp Pro Trp Gln Val Ser Ile Thr Tyr
    50                  55                  60

Glu Gly Val His Val Cys Gly Gly Ser Leu Val Ser Glu Gln Trp Val
65                  70                  75                  80

Leu Ser Ala Ala His Cys Phe Pro Ser Glu His His Lys Glu Ala Tyr
                85                  90                  95

Glu Val Lys Leu Gly Ala His Gln Leu Asp Ser Tyr Ser Glu Asp Ala
            100                 105                 110

Lys Val Ser Thr Leu Lys Asp Ile Ile Pro His Pro Ser Tyr Leu Gln
        115                 120                 125

Glu Gly Ser Gln Gly Asp Ile Ala Leu Leu Gln Leu Ser Arg Pro Ile
    130                 135                 140

Thr Phe Ser Arg Tyr Ile Arg Pro Ile Cys Leu Pro Ala Ala Asn Ala
145                 150                 155                 160

Ser Phe Pro Asn Gly Leu His Cys Thr Val Thr Gly Trp Gly His Val
                165                 170                 175

Ala Pro Ser Val Ser Leu Leu Thr Pro Lys Pro Leu Gln Gln Leu Glu
            180                 185                 190

Val Pro Leu Ile Ser Arg Glu Thr Cys Asn Cys Leu Tyr Asn Ile Asp
        195                 200                 205

Ala Lys Pro Glu Glu Pro His Phe Val Gln Glu Asp Met Val Cys Ala
    210                 215                 220

Gly Tyr Val Glu Gly Gly Lys Asp Ala Cys Gln Gly Asp Ser Gly Gly
225                 230                 235                 240

Pro Leu Ser Cys Pro Val Glu Gly Leu Trp Tyr Leu Thr Gly Ile Val
                245                 250                 255

Ser Trp Gly Asp Ala Cys Gly Ala Arg Asn Arg Pro Gly Val Tyr Thr
            260                 265                 270

Leu Ala Ser Ser Tyr Ala Ser Trp Ile Gln Ser Lys Val Thr Glu Leu
        275                 280                 285

Gln Pro Arg Val Val Pro Gln Thr Gln Glu Ser Gln Pro Asp Ser Asn
    290                 295                 300

Leu Cys Gly Ser His Leu Ala Phe Ser Ser Ala Pro Ala Gln Gly Leu
305                 310                 315                 320

```
Leu Arg Pro Ile Leu Phe Leu Pro Leu Gly Leu Ala Leu Gly Leu Leu
            325                 330                 335

Ser Pro Trp Leu Ser Glu His
            340

<210> SEQ ID NO 3
<211> LENGTH: 23
<212> TYPE: DNA
<213> ORGANISM: Homo sapiens

<400> SEQUENCE: 3
acttgagcca ctccttcctt cag                                          23

<210> SEQ ID NO 4
<211> LENGTH: 22
<212> TYPE: DNA
<213> ORGANISM: Homalozoon vermiculare

<400> SEQUENCE: 4
ctgatggtcc caaaaagcac ac                                           22
```